(12) United States Patent
Bevis

(10) Patent No.: US 7,808,638 B2
(45) Date of Patent: Oct. 5, 2010

(54) SCATTEROMETRY TARGET AND METHOD

(75) Inventor: Christopher F. Bevis, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 12/121,428

(22) Filed: May 15, 2008

(65) Prior Publication Data
US 2009/0015821 A1 Jan. 15, 2009

Related U.S. Application Data

(60) Provisional application No. 60/949,803, filed on Jul. 13, 2007.

(51) Int. Cl.
*G01B 11/00* (2006.01)
(52) U.S. Cl. .................................................... 356/401
(58) Field of Classification Search ........................ None
See application file for complete search history.

(56) References Cited

U.S. PATENT DOCUMENTS

| 6,767,680 | B2 * | 7/2004 | Schulz ........................ 430/30 |
| 6,982,793 | B1 * | 1/2006 | Yang et al. .................. 356/401 |
| 7,242,477 | B2 | 7/2007 | Mieher et al. |
| 7,280,212 | B2 | 10/2007 | Mieher et al. |
| 7,289,213 | B2 | 10/2007 | Mieher et al. |
| 7,298,481 | B2 | 11/2007 | Mieher et al. |
| 7,301,634 | B2 | 11/2007 | Mieher et al. |
| 7,317,531 | B2 | 1/2008 | Mieher et al. |
| 2002/0107650 | A1 * | 8/2002 | Wack et al. .................. 702/81 |
| 2004/0008349 | A1 * | 1/2004 | Norton ........................ 356/369 |
| 2004/0233440 | A1 | 11/2004 | Mieher et al. |
| 2004/0233442 | A1 | 11/2004 | Mieher et al. |
| 2005/0195398 | A1 | 9/2005 | Adel et al. |
| 2006/0066855 | A1 * | 3/2006 | Boef et al. .................. 356/401 |
| 2007/0052113 | A1 * | 3/2007 | Marokkey et al. ........... 257/797 |
| 2007/0229829 | A1 | 10/2007 | Kandel et al. |

OTHER PUBLICATIONS

U.S. Appl. No. 11/724,905, filed Mar. 15, 2007.
U.S. Appl. No. 11/926,603, filed Oct. 29, 2007.

* cited by examiner

*Primary Examiner*—Tarifur Chowdhury
*Assistant Examiner*—Gordon J Stock, Jr.
(74) *Attorney, Agent, or Firm*—Suiter Swantz pc llo

(57) ABSTRACT

Embodiments of the invention include a SCOL targeting groups configured to increase target to target separation and thereby increase target utility to simultaneous exposures to multiple illumination dots and associated inspection methodologies. The embodiments of the invention further relate to apparatus for projection simultaneous illumination dots onto different targets of the same targeting group on a wafer to conduct multiple simultaneous target inspections. Embodiments of the invention further relate to methods used to inspect SCOL targets using simultaneous illumination dots directed onto different targets of the same targeting group to conduct multiple simultaneous target inspections.

4 Claims, 7 Drawing Sheets

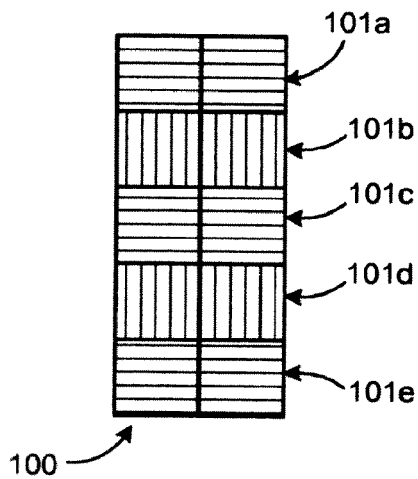
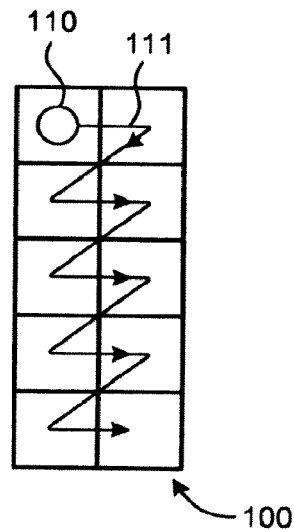
Fig. 1(a) (prior art)
Fig. 1(b) (prior art)
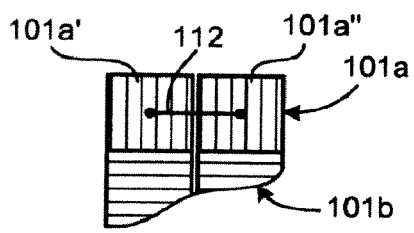
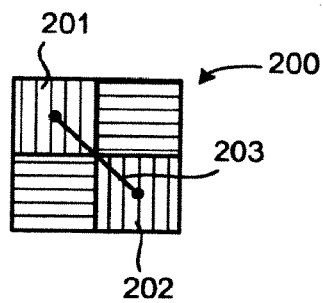
Fig. 1(c) (prior art)
Fig. 2(a)
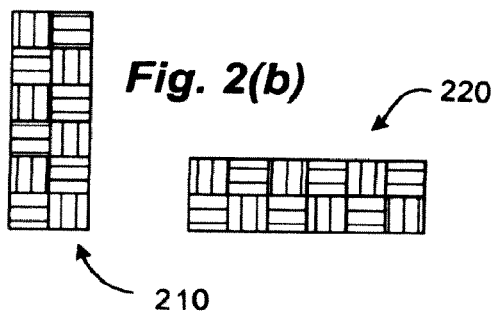
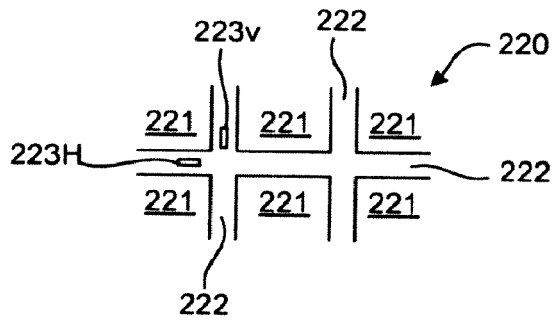
Fig. 2(b)
Fig. 2(c)

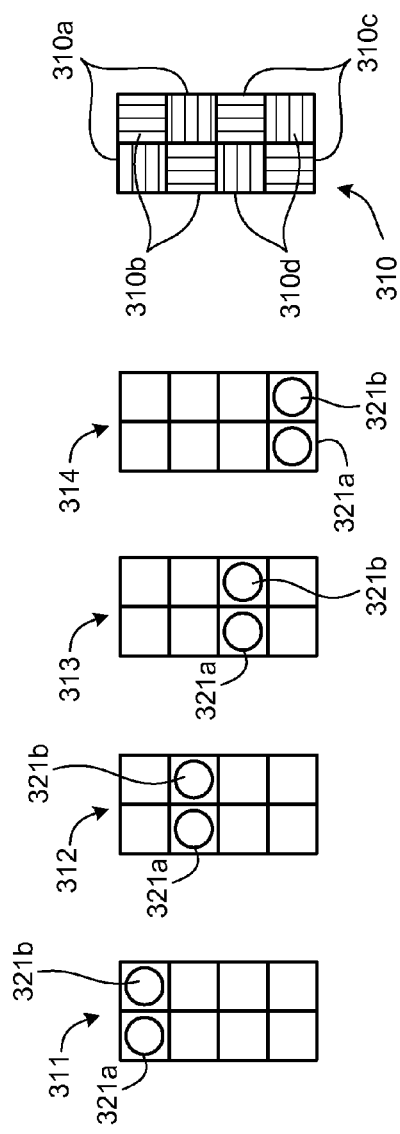
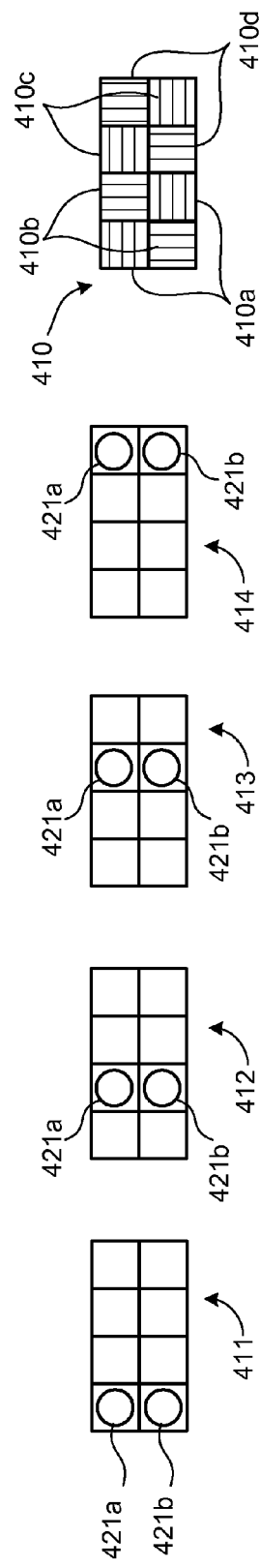
Fig. 3
Fig. 4

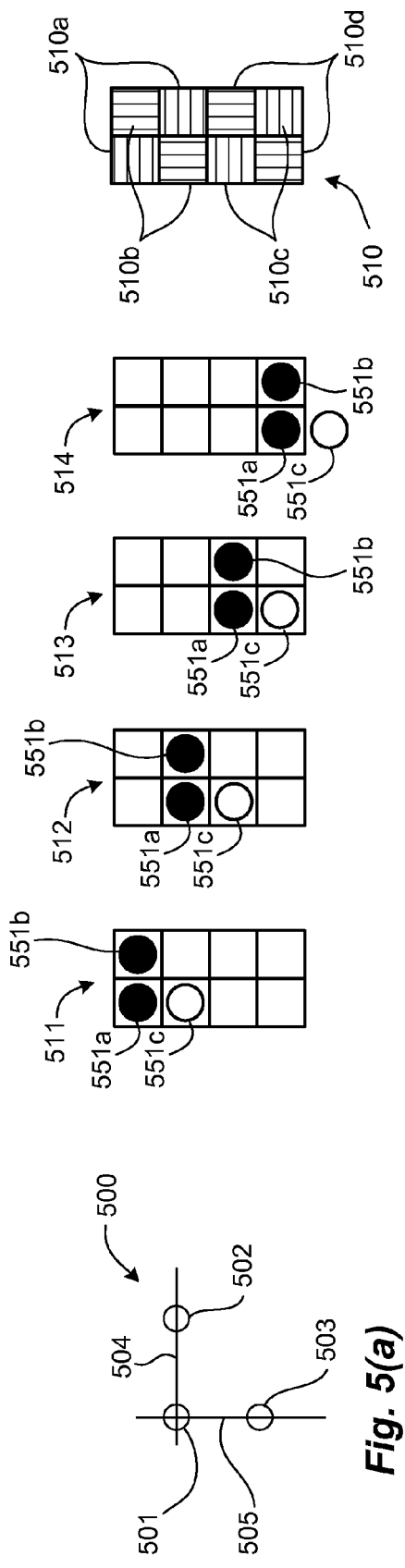
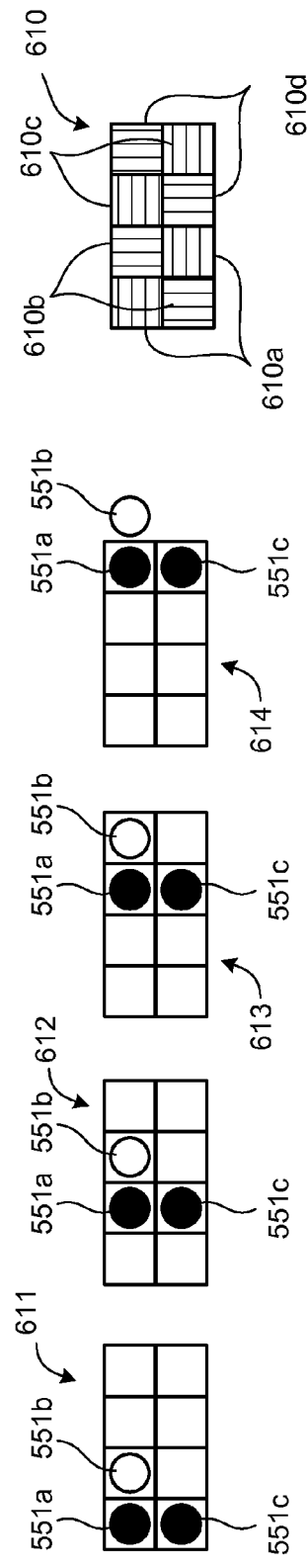

SCATTEROMETRY TARGET AND METHOD

CROSS REFERENCE TO RELATED APPLICATIONS

This application claims priority under 35 USC §119.(e) to U.S. Provisional Patent Application No. 60/949,803, filed Jul. 13, 2007, entitled "SCATTEROMETRY TARGET AND METHOD", which is incorporated herein by reference in its entirety.

This application is also related to the following U.S. patent applications and Patents: U.S. Pat. No. 7,317,531, entitled "APPARATUS AND METHODS FOR DETECTING OVERLAY ERRORS USING SCATTEROMETRY"; U.S. Patent Publication No.: 2004/0233440, entitled "APPARATUS AND METHODS FOR DETECTING OVERLAY ERRORS USING SCATTEROMETRY"; U.S. Pat. No. 7,298,481, entitled "APPARATUS AND METHODS FOR DETECTING OVERLAY ERRORS USING SCATTEROMETRY"; U.S. Pat. No. 7,280,212, entitled "APPARATUS AND METHODS FOR DETECTING OVERLAY ERRORS USING SCATTEROMETRY"; U.S. Pat. No. 7,301,634, entitled "APPARATUS AND METHODS FOR DETECTING OVERLAY ERRORS USING SCATTEROMETRY"; U.S. Patent Publication No.: 2004/0233442, entitled "APPARATUS AND METHODS FOR DETECTING OVERLAY ERRORS USING SCATTEROMETRY"; U.S. Pat. No. 7,242,477, entitled "APPARATUS AND METHODS FOR DETECTING OVERLAY ERRORS USING SCATTEROMETRY"; U.S. Pat. No. 7,289,213, entitled "APPARATUS AND METHODS FOR DETECTING OVERLAY ERRORS USING SCATTEROMETRY"; U.S. Patent Publication No.: 2005/0195398, entitled "CONTINUOUSLY VARYING OFFSET MARK AND METHODS OF DETERMINING OVERLAY"; U.S. Patent Publication No.: 2007/0229829, entitled "APPARATUS AND METHODS FOR DETECTING OVERLAY ERRORS USING SCATTEROMETRY"; U.S. patent application Ser. No. 11/724,905, entitled "INSPECTION METHODS AND SYSTEMS FOR LITHOGRAPHIC MASKS"; and U.S. patent application Ser. No. 11/926,603, entitled "APPARATUS AND METHODS FOR DETECTING OVERLAY ERRORS USING SCATTEROMETRY". All of the foregoing applications and patents are hereby incorporated by reference in their entirety.

TECHNICAL FIELD

The invention described herein relates generally to semiconductor fabrication and inspection technologies. In particular, the invention refers improved scatterometry targets and associated inspection methods enabling a high degree of sensitivity to parameters of interest and methodologies for measuring such targets. Particularly, the invention refers to target embodiments wherein a patterned target array includes an intentionally introduced defect that enables measurements of the target to have increased sensitivity to a parameter of interest that is related to the defect.

BACKGROUND

As is well-understood in the art, periodic scatterometry targets are used to obtain accurate measurements of target features. Such targets include massive arrays of uniformly constructed and uniformly spaced periodic features arranged to provide the best possible targeting information. Typical prior art example targets include periodic gratings or periodically configured higher dimensional target arrays comprised of a plurality of uniformly spaced and sized metrology features.

Such periodic targeting structures typically feature two layers of similarly oriented periodic gratings formed one over the other. Typically, the layers are designed with a specified predetermined offset with respect to each other. This enables scattering signals to be generated when illuminated by a light beam. A comparison of the actual signal produced with the expected scattering signal enables highly accurate overlay metrology measurements to be made.

Generally, several different targets sequentially illuminated and measurements of the scattering signals are then used to make overlay measurements. Typically, the several targets each having different offsets which enable accurate overlay measurements to be made. These measurements enable a determination of alignment accuracy to be obtained for the various fabrication processes used to form the layers of a semiconductor wafer.

In general, prior art targeting arrays employ several different targets having a range of offsets (offsets between the top and bottom layer gratings of the target) to enable accurate overlay measurements to be made. Typical targeting arrays include a plurality of scatterometry targets arranged in complementary target pairs. A complementary target pair is a pair of targets that have an offset between gratings of a first amount (say an offset of "x" Ångstroms (Å) in a "positive" direction and a complementary offset of the same distance (say an offset of "-x" Å) in an opposite direction (i.e. a "negative" offset) to form a complementary pair of targets. Such a target is said to have a symmetrical scatterometry overlay (SCOL) offset.

Examples of prior art systems which rely on scatterometry techniques can be found in U.S. Pat. Nos. 5,867,276; 5,963,329; and 5,739,909. These patents describe using both spectrophotometry and spectroscopic ellipsometry to analyze periodic structures and are incorporated herein by reference. Another useful background reference describing many such scatterometry approaches is disclosed in the U.S. patent application Ser. No. 11/525,320 entitled "Apparatus and Methods for Detecting Overlay Errors Using Scatterometry" also incorporated by reference herein. Numerous other related approaches are also well known in the art.

FIG. 1(a) is a simplified diagram illustrating a commonly known targeting array 100. In most targeting arrangements known today these complementary target pairs are arranged vertically or horizontally adjacent pairs. The depicted illustration includes five adjacent complementary target pairs (101a, 101b, 101c, 101d, and 101e) arranged in a series of rows where each target in a complementary target pair is horizontally adjacent to the other target of the pair. Each target of the pair has gratings that are arranged parallel to the gratings of the other target in the pair. As mentioned above, each target in the complementary pair features a predetermined positive and negative offset. In FIG. 1(c), for example, targets 101a' and 101a" represent "x targets" (having gratings arranged parallel to the x-axis). Correspondingly, for example, FIG. 1(a) targets 101b' and 101b" represent "y targets" (having gratings arranged parallel to the y-axis).

FIG. 1(b) provides an illustration of a common illumination approach used in conjunction with the targeting arrangement depicted in FIG. 1(a). An illumination beam is directed onto on of the targets of the first complementary pair 101a to form an illumination spot 110 which is then moved to each target (e.g., following path 111) in the targeting array 100 to generate scattering signals that are collected and analyzed to generate overlay metrology measurements.

One unfortunate limitation of such a targeting arrangement deals with the fact that the illumination spot 110 is actually an Airy disk having portions of the optical signal that extend beyond the boundaries of each target and have the potential to generate large amounts of signal "contamination" by illuminating considerable portions of nearby complementary targets. Such signal contamination occurs when the optical signal of the illumination spot 110 extends onto the adjacent target of the complementary pair thereby generating scattering signal from the adjacent target. Such "cross-talk" can seriously degrade the fidelity and information content of the scattering signal. This is a serious problem that will be discussed in greater detail below.

An additional limitation of this existing approach is that it is slow. A single spot must be directed to each target on a targeting arrangement and then to each target on the entire wafer (there can be 100's or 1000's of such targets). Thus, it can take a considerable time to inspect an entire wafer.

Therefore, although such existing processes and tools are suitable for their intended purposes, improvements can be made. The present invention seeks to go beyond the limitations and structural shortcomings of existing technologies.

SUMMARY OF THE INVENTION

In accordance with the principles of the present invention, improved scatterometry targets and methods for its use are disclosed.

In general, the present invention is directed toward targets, devices, and methods enabling simultaneous illumination and data collection for more than one scatterometry overlay (SCOL) metrology target at a time.

In one embodiment, the inventive embodiments include a scatterometry overlay targeting group formed on a substrate that includes a plurality of SCOL targets arranged in complementary pairs of SCOL targets, each target in a complementary pair having a parallel grating orientation and a symmetrical SCOL offset, the targets in each complementary pair are arranged in a configuration that increases a center to center distance between each target in the complementary pair relative to a target pair configuration of adjacent and horizontally or vertically arranged target pairs. In some embodiments, the complementary target pairs are disposed in a diagonal arrangement. Other embodiments include target groups arranged in a checkerboard pattern of alternating diagonally disposed SCOL targets such that each SCOL target of a complementary target pair is arranged diagonally with respect to another SCOL target of the pair.

Another SCOL target group embodiment comprises a plurality of SCOL targets arranged staggered rows of targets extending along a long axis of the target group. A first row of targets is arranged next to a second row of targets with the staggered arrangement being such that the targets of the first row are offset relative to the targets of the second row by a full target dimension enabling a pair of diagonally disposed illumination dots to be directed onto one target from each row at a 45 degree angle from the long axis of the target group.

Another embodiment of the invention concerns a method of conducting simultaneous scatterometry measurements using a plurality of illuminating light beams. A substrate is provided with SCOL target group having a plurality of SCOL targets. At least two illumination beams are simultaneously directing onto the targeting group to form illumination dots that simultaneously illuminate at least two targets of the targeting group to generate associated scattering signals which are measured and processed to obtain scatterometry metrology information. Such embodiments include methods that employ three-beam illumination dot patterns. Also, embodiments using diagonally disposed illumination dots having beam polarization orientation at ±45 degrees relative to target grating orientations are also disclosed herein.

Another embodiment of the invention comprises a scatterometry overlay inspection apparatus that includes an illumination system configured to simultaneously generate at least two light beams. The apparatus further includes an optical system that enables simultaneous direction of the at least two light beams onto at least two targets of a scatterometry targeting array formed on the wafer to generate at least two associated scattering signals. The wafer being secured to an examination platform that enables movement of the wafer under inspection. The apparatus further includes another optical system configured to direct the at least two associated scattering signals into a detection system. The detection system can include analysis systems if desired.

Other aspects and advantages of the invention will become apparent from the following detailed description and accompanying drawings which illustrate, by way of example, the principles of the invention.

BRIEF DESCRIPTION OF THE DRAWINGS

The following detailed description will be more readily understood in conjunction with the accompanying drawings, in which:

FIGS. 1(a)-1(b) illustrates prior art scatterometry targets and associated methods of inspection.

FIG. 1(c) is a simplified illustration of a portion of a prior art scatterometry target that shows a center to center distance between prior art targets.

FIG. 2(a) is a simplified depiction of a portion of an inventive scatterometry target that shows the increased center to center distance between inspected targets in accordance with the principles of the invention.

FIG. 2(b) is a simplified diagram illustrating a checkerboard targeting structure of the present invention that incorporate diagonally arranged targets having alternating grating orientations in accordance with an embodiment of the invention.

FIG. 2(c) is a simplified diagram illustrating a portion of a wafer surface showing device areas and the associated saw streets as well as targeting groups positioned in the saw streets in accordance with some embodiments of the invention FIGS. 3 & 4 are simplified diagrams of horizontal and vertical targeting groups illustrating various inspection embodiments utilizing two spot simultaneous illumination in accordance with an embodiment of the invention.

FIG. 5(a) is a simplified illustration of a three beam illumination dot pattern constructed in accordance with the principles of the invention.

FIGS. 5(b) & 6 are simplified diagrams of horizontal and vertical targeting groups illustrating various inspection embodiments utilizing three spot illuminations to inspect target pairs in accordance with an embodiment of the invention.

It is to be understood that in the drawings like reference numerals designate like structural elements. Also, it is understood that the depictions in the Figures are not necessarily to scale.

DETAILED DESCRIPTION OF THE INVENTION

Figure 7:
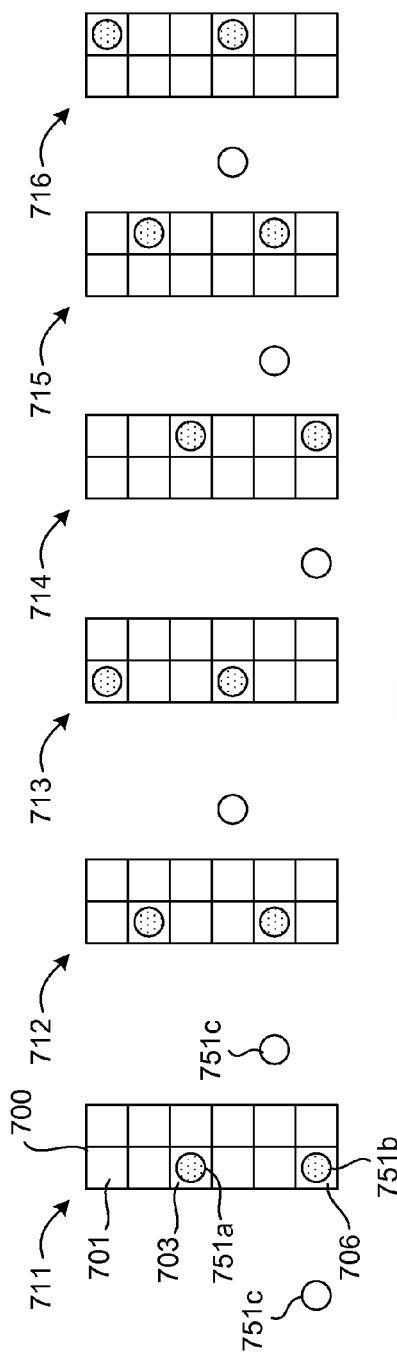
FIGS. 7 & 8 are simplified diagrams of horizontal and vertical targeting groups illustrating various inspection embodiments utilizing three spot illuminations with substantially spaced apart dots to inspect target pairs in accordance with an embodiment of the invention.

The present invention has been particularly shown and described with respect to certain embodiments and specific features thereof. The embodiments set forth hereinbelow are to be taken as illustrative rather than limiting. It should be readily apparent to those of ordinary skill in the art that various changes and modifications in form and detail may be made without departing from the spirit and scope of the invention.

In general, the present invention encompasses enhanced scatterometry targets and illumination approaches used to enable improved scatterometry methodologies as disclosed herein. Such target embodiments as disclosed herein can enable increased inspection speed, as well as increased accuracy and sensitivity in multi-beam inspection methodologies. Target configurations disclosed herein enable multiple targets from the same targeting group to be inspected simultaneously. In particular, using targeting group embodiments disclosed herein, more than one target can be illuminated at a time to generate at least two simultaneously generated scattering signals that feature reduced cross-talk between the scattering signals due to increased spacing between the targets of a targeting group. Additionally, the novel targeting group arrangements discussed herein enable such increased spacing between complementary target pairs without increasing the area of the targeting group. This is a very advantageous feature. In particular, targeting groups and illumination dot configurations arranged to have a separation between illumination dots (and inspected targets) of at least $2\sqrt{2}a$ (where each target is about 2a wide) provide improved target information when used in a multi-beam inspection approach as disclosed herein.

FIG. 1(c) schematically depicts a portion of the targeting array 100 which illustrate, in this example, complementary target pairs 101a and 101b. For illustration purposes, the center to center distance 112 between the targets of complementary pair 101a are abstractly identified as distance 2a (the same as the width of each of the targets). In such an arrangement, cross talk from the light spot directed onto target 101a' partially illuminates target 101a" which is a complementary target. This spill over light generates particularly troublesome contamination when it illuminates the complementary target 101a" thereby producing a scattering signal capable of degrading the scattering signal from target 101a'.

To clarify, the applicants mean "complementary target pairs" to be a pair of targets having a symmetrical offset between the grating layers of the targets. For example, one example complementary target pair includes a target having an offset of +x (where "x" is a displacement distance between grating layers of a target in an "x" direction) and another related target having an offset of −x (of the same magnitude but opposite direction). A target pair with an offset of x and 2x respectively is not complementary or symmetric. And a target pair with offsets of, for example, x and 2y is an unrelated target pair. Then inventor point out that the principles of the invention can be applied to the simultaneous inspection of complementary target pairs, asymmetric target pairs (e.g., offsets of x & 2x) or unrelated target pairs.

In continuation, the inventors have determined that due to the nature of an Airy disk (such as is formed by illumination beams of the present invention to generate the light spots) only a small increase in separation distance between the two complementary pairs can result in a substantial reduction in cross-talk. FIG. 2(a) depicts on implementation of a targeting scheme in accordance with the principles of the invention. FIG. 2(a) depicts a simplified scatterometry overlay targeting group (also referred to as a scatterometry targeting array) 200. This depicted targeting arrangement (200) is simplified to an example having only four targets. Each target comprises a scatterometry overlay (SCOL) target. As before, the targeting arrangement is configured with complementary target pairs arranged with parallel overlay gratings having differing complementary offsets (in this embodiment positive and negative offsets of equal magnitude). In this embodiment, the inventors have changed the positional relationship between the between the two targets (201, 202) of the first complementary pair of targets (analogous to 101a', 101a" as depicted in e.g., FIG. 1(c)). Thus, instead of being horizontally (or vertically) adjacent to each other they are now diagonally disposed with respect to each other. This carries through for all other complementary target pairings. Each target is arranged diagonally from its complementary target in the pair. The idea being to increase the center to center distance between the targets of each complementary pair. The inventors contemplate other arrangements that also increase the distance between the targets of a complementary pair. This increased distance helps to decrease cross-talk signal contamination from nearby complementary targets. Some aspects of these embodiments will be discussed in more detail below.

Returning to the embodiment depicted in FIG. 2(a), for the same size targets, the center to center distance 203 between the targets (201, 202) of a complementary target pair is now $2\sqrt{2}a$ rather than 2a thus increasing the distance between targets by over 40% and obtaining far less cross talk between complementary target pairs. In embodiments of the invention targets of any size may be used. However, common implementations typically employ targets ranging from about 20 μm×20 μm to about 40 μm×40 μm in size.

The same arrangement of pairs can be established for all complementary target pairs in a scatterometry overlay targeting group. When extended to an entire scatterometry overlay targeting group, a checkerboard pattern of alternating diagonally arranged complementary target pairs can be formed. One simplified example is shown in FIG. 2(b) wherein 210 depicts a vertically arranged targeting group and 220 depicts a horizontally arranged targeting group. Commonly, such targeting groups are positioned in the saw streets of a wafer and such vertical and horizontal orientations are helpful to accommodate positioning in associated vertical and horizontal saw streets.

Due to the increased distance between the centers of the targets of the complementary target pairs, such target groups exhibit increased suitability for inspection using simultaneous illumination of multiple targets with multiple beams to obtain metrology measurements. Due to the increased distance between the target centers, simultaneous illumination of complementary target pairs results in less cross-talk between the scattering signals produced by the illuminated target pairs. Thus, "checker board" patterns of targets (i.e., those having interlaced diagonally arranged complementary target pairs) such as the examples shown in FIGS. 2(a) & 2(b) provide increased suitability for such simultaneous illumination of targets with a multiple beam exposure apparatus. Such will be discussed in more detail below.

FIG. 2(c) illustrates and enable a discussion of targeting group positioning. In general, the target groups of the present invention have a long axis and short axis. The long axis extending a longer distance than an associated short axis. This is easily understood with respect to FIG. 2(b) where the long and short axis of two target groups can be seen. The long axis extends down the length of the longest axis in the targeting group. Frequently, the targeting groups are placed in areas of a wafer that are not subject patterning for circuit elements. One particularly common location for such target groups are the saw streets between devices on the wafer. As saw streets are becoming narrower and narrower, there is pressure to form targeting structures that are narrow. Such is the case in the present invention. FIG. 2(c) depicts a portion of a wafer surface 220. Depicted are a number of device areas 221 where device elements are to be formed during fabrication. These device areas 221 are defined by horizontal and vertical saw streets 222 that separate the surface of the wafer. In the saw streets are positioned a number of targeting groups such as are disclosed in detail throughout this patent. One vertically arranged target group 223v is positioned in a vertically disposed saw street 222 so that the long axis of the vertical targeting group 223v extends vertically up the saw street. A corresponding horizontally arranged target group 223H is positioned in a horizontally disposed saw street 222 so that the long axis of the horizontal targeting group 223H extends horizontally across the saw street 222. Such is a typical arrangement of the various target embodiments of the present invention. During final fabrication steps the target groups are destroyed by cuts made in the saw streets to separate the devices.

In implementing this targeting group an inspection apparatus using two or more illumination beams can be used to great advantage. FIGS. 3 & 4 illustrate one possible illumination approach using at least two illumination beams to illuminate the targets of a targeting group. Referring to FIG. 3, an example targeting group 310 that extends longitudinally in the vertical direction (here along the y-axis) is depicted. The targets are arranged with some gratings parallel to an x-axis and some gratings parallel to a y-axis. The complementary target pairs 310a, 310b, 310c, 310d, are each arranged so that the complementary pairs of targets are arranged diagonal to each other to form a checkerboard pattern.

Each of the four exposure diagrams 311, 312, 313, 314 depicts the targeting group as it is subject to various illuminations to obtain metrology information. A first illumination 311 is performed using two light spots 321a, 321b directed onto the targeting group of 311. One target from pair 310a and one target from pair 310b are each simultaneously illuminated with a spot (e.g., 321a, 321b). An example spot 321a can be produced by a laser, for example, having a diameter of about 20 μm to illuminate a target having a dimension of, for example, 30 μm×30 μm. Two scattering signals are produced and can be collected using appropriate detector apparatus. The beams (spots 321a, 321b) advance down the targeting group to another set of targets (which can be adjacent) to generate a second set of scattering signals as depicted in diagram 312. Again, two additional scattering signals are produced and can be collected using appropriate detector apparatus. Further, the beams (spots 321a, 321b) advance down the targeting group to another set of targets to generate another set of scattering signals as depicted in diagram 313.

As before, the two additional scattering signals are collected using a detector apparatus. This continues until the entire target group is measured. Finally, the beams (spots 321a, 321b) examine the last targets desired to be measured of the targeting group to generate a last set of scattering signals as depicted in diagram 314. The final two scattering signals are collected using appropriate detector apparatus. This completes the examination of a vertically oriented targeting group 310. The simultaneously illuminated targets can be a complementary target pair (i.e., symmetrical but offset in opposite directions, e.g., +x, −x), an asymmetric target pair (i.e., offsets in the same direction but having different offset magnitudes e.g., +x, −2x), or unrelated target pairs (e.g., 2y, −x).

Typically, a wafer also includes horizontally oriented targeting groups. Such are generally situated in the horizontal saw streets. In order to balance certain effects, the orientation of the illumination beams can be rotated to capture the targets appropriately. Referring to FIG. 4, an example targeting group 410 that extends longitudinally in the horizontal direction (here along the x-axis) is depicted. As before, targets are arranged having some gratings parallel to an x-axis and some gratings parallel to a y-axis. The complementary target pairs 410a, 410b, 410c, 410d, are each arranged so that the complementary pairs of targets are arranged diagonal to each other to form another checkerboard pattern.

Another group of four exposure diagrams 411, 412, 413, 414 depicts the targeting group as it is illuminated to obtain metrology information. A first illumination 411 is performed using two light spots 421a, 421b directed onto the targeting group of 411. The pair of illumination spots (e.g., 421a, 421b) each simultaneously illuminate a pair of targets (e.g., a target selected from pair 410a and a target selected from pair 410b). As before, a laser or other light source can generate the appropriate spot to generate two scattering signals (one associated with each target) that are collected using appropriate detector apparatus. The beams (spots 421a, 421b) advance horizontally across the targeting group to another set of targets (which can be adjacent) to generate a second set of scattering signals as depicted in diagram 412. Two additional scattering signals are produced and collected. The process continues with the beams (spots 421a, 421b) advancing across the targeting group to another set of targets to generate another set of scattering signals as depicted in diagram 413. As before, two additional scattering signals are produced and collected using a detector apparatus. This continues until the entire target group is measured or until a desired number of targets are inspected. Finally, the beams (spots 421a, 421b) examine the last targets to be measured from the targeting group to generate a last set of scattering signals as depicted in diagram 414. The final two scattering signals are collected using appropriate detector apparatus. This completes the examination of a horizontally oriented targeting group 410. The inventors specifically point out that the specific details of this implementation can be varied considerably and still fall with the bounds of the invention. For example, the illumination order can be varied at will. Additionally, the simultaneously illuminated targets can be any pair of targets (e.g., a complementary target pair, an asymmetric target pair, or an unrelated target pair).

The inventors contemplate another very advantageous implementation of the invention which is described as follows. In implementing this targeting group an inspection apparatus using three or more illumination beams can be used to great advantage eliminate the need to rotate the beams to change the horizontal and vertical illumination orientations. FIGS. 5(a), 5(b), & 6 illustrate aspects of this illumination approach.

FIG. 5(a) illustrates one example of a three beam illumination dot pattern 500. In the depicted embodiment, an L-shaped pattern of three illumination spots (501, 502, 503) is used to illuminate targets. The pattern includes a first illumination axis 504 that passes through two dots (here 501, 502) and a perpendicular second illumination axis 505 that passes through two dots (here 501, 503). The perpendicular dot arrangement enables easy adaptation to inspection of perpendicularly arranged target groups. Such a configuration requires no change or adjustment of the optics to inspect either set of target groups. One example embodiment can employ laser generated dots having an approximated diameter of about 20 µm. As is known to those of ordinary skill, different light sources and beam dot diameters can also be used.

The following illustrations show a few possible implementations of a three beam illumination pattern. Referring to FIG. 5(b), an example targeting group 510 (being identical to group 310 of the example of FIG. 3) extends in the vertical direction. As before, x and y oriented gratings can be used. Complementary target pairs 510a, 510b, 510c, 510d, are each arranged so that the complementary pairs of targets are arranged diagonal to each other to form a checkerboard pattern. Although only four pairs are shown here, embodiments having fewer or more pairs are expressly contemplated by the inventors.

Four exposure diagrams 511, 512, 513, 514 depict the path of the illumination beams as the illuminate the targeting group. In this embodiment, an L-shaped pattern of three illumination spots (551a (dark spot), 551b (dark spot), 551c (white spot)) is used to illuminate the targets. A first illumination 511 is performed using the light spots directed onto the targeting group of 511. One target from pair 510a and one target from pair 510b are each simultaneously illuminated with a spot (e.g., 551a, 551b). As before, example spots (e.g., 551a) can be produced by a laser or other suitable light source having, for example, a diameter of about 20 µm to illuminate a target having a dimension of, for example, 30 µm×30 µm. Three scattering signals are produced but only the signals corresponding to the two beams 551a, 551b (the dark spots) are collected with a detector apparatus. The three spots advance down the targeting group to another set of targets and another set of scattering signals is collected (e.g., as associated with the dark spots 551a, 551b) as depicted in diagram 512. The spots further advance down the targeting group to another set of targets to generate another set of scattering signals as depicted in diagram 513. As before, two scattering signals (associated with dark spots 551a, 551b) are collected using a detector apparatus. This continues until the entire target group is measured. Finally, the spots illuminate the last targets desired to be measured of the targeting group to generate and collect a last set of two scattering signals as depicted in diagram 514. The spot 551c no longer illuminates a target, but as the scattering signal generated by this spot is not collected at this time it is not relevant. This completes the examination of a vertically oriented targeting group 510.

Because the L-shaped three beam configuration is used, the orientation of the illumination beams does not need to be rotated to capture the horizontally extending targets. This is highly advantageous because no movement and no adjustment of the beams is required. Referring to FIG. 6, an example horizontally extending targeting group 610 (that is essentially identical to the example 410 of FIG. 4) is depicted. As before, targets are arranged having gratings parallel to the x-axis and y-axis. The complementary target pairs 610a, 610b, 610c, 610d, are each arranged so that the complementary pairs of targets are arranged diagonal to each other to form another checkerboard pattern. The inventors specifically point out that the specific details of this implementation can be varied considerably and still fall with the bounds of the invention. For example, the illumination order can be varied at will. Additionally, the simultaneously illuminated targets can be any pair of targets (e.g., a complementary target pair, an asymmetric target pair, or an unrelated target pair).

Another group of four exposure diagrams 611, 612, 613, 614 depicts the targeting group as it is illuminated to obtain metrology information. A first illumination 611 is performed using the L-shaped pattern of three illumination spots (551a (dark spot), 551b (white spot), 551c (dark spot)) to illuminate the targets. One target from pair 610a and one target from pair 610b are each simultaneously illuminated with a spot (e.g., 551a, 551c). Only this time it will be scattering from spot 551b (white spot) that will be ignored in these measurements. Thus, the pair of illumination spots (551a, 551c) each simultaneously illuminate a target from the targeting group. As before, a laser or other light source can generate the appropriate spot to generate scattering signals, two of which (the ones associated with 551a and 551c) are collected using appropriate detector apparatus. The three beams advance horizontally across the targeting group to another set of targets (which can be adjacent) to generate scattering signals as depicted in diagram 612. Two additional scattering signals are collected (associated with 551a, 551c). The process continues with the three spots advancing across the targeting group to another set of targets to generate another set of scattering signals as depicted in diagram 613. As before, two additional scattering signals are produced and collected using a detector apparatus. This continues until the entire target group is measured. Finally, the spots illuminate the last targets desired to be measured of the targeting group to generate and collect a last set of two scattering signals as depicted in diagram 614. The spot 551b no longer illuminates a target, but as the scattering signal generated by this spot is not collected at this time it is not relevant. This completes the examination of a horizontally oriented targeting group 610.

Figure 8:
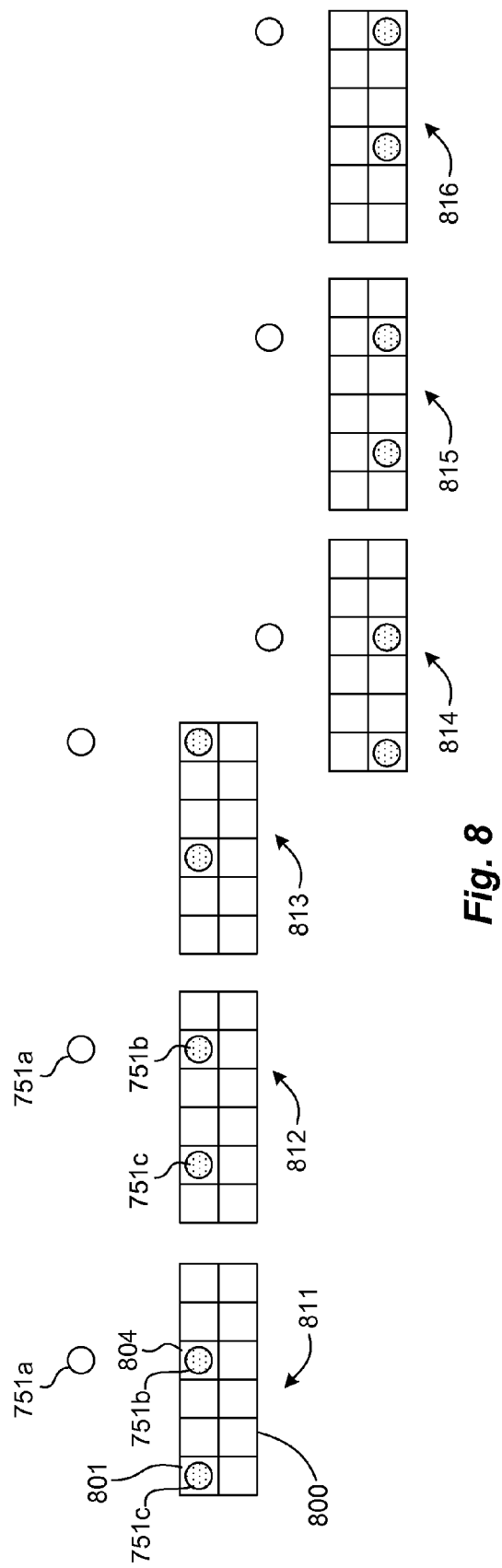

In another implementation, a larger distance between the two illumination dots can be employed to substantially reduce the cross talk between the simultaneous scattering signals generated. FIGS. 7 & 8 illustrate one possible illumination approach using at least two widely separated illumination dots to illuminate the targets of a targeting group. Referring to FIG. 7, an example targeting group 700 is processed through an example inspection sequence. The depicted example targeting group 700 extends longitudinally in the vertical direction (here along the y-axis). As with other depicted embodiments, the targets are arranged with some gratings parallel to an x-axis and some gratings parallel to a y-axis. In these embodiments, the target group is extended to enable wider separation between the inspected targets. In the depicted example, the targets (e.g. 701) are sized at $2a \times 2a$ (e.g., 30 µm×30 µm) and the center to center separation between targets is greater than $2\sqrt{2}\alpha$ (shown here as a separation of about 6 a). In such an embodiment, the targeting group can be arranged in any desired manner so long as all desired targets can be inspected.

In implementing this targeting group 700 an inspection apparatus using three or more illumination beams can be used. FIG. 7 illustrates an example targeting group 700 that extends in the vertical direction. As before, x and y oriented gratings are used. The targets are arranged so that the desired target pairs (here 703, 706) of target 700 have the necessary spacing. Although only six pairs are shown here, embodiments having fewer or more pairs are expressly contemplated by the inventors.

The six exposure diagrams 711, 712, 713, 714, 715, 716 depict the path of the illumination beams as the illuminate the targeting group. In this embodiment, an L-shaped pattern of three illumination spots (751*a* (dark spot), 751*b* (dark spot), 751*c* (white spot)) is used to illuminate the targets. A first illumination 711 is performed using the light spots directed onto the targeting group of 711. Targets 703 and 706 are each simultaneously illuminated with a spot (e.g., 751*a*, 751*b*). As before, example spots (e.g., 751*a*) can be produced by suitable light sources. Only the scattering signals corresponding to the two beams 751*a*, 751*b* (the dark spots) are collected with a detector apparatus. The three spots advance over the targeting group to another set of targets and another set of scattering signals is collected (e.g., as associated with the dark spots 751*a*, 751*b*) as depicted in diagram 712. The spots further advance down the targeting group to another set of targets to generate another set of scattering signals as depicted in diagram 713. As before, two scattering signals (associated with dark spots 751*a*, 751*b*) are collected using a detector apparatus. The targeting apparatus can switch to a different column of targets (e.g., as depicted in diagrams 714-716) and continue until the entire target group or all the desired targets are inspected. Finally, in this example, the spots illuminate the last targets desired to be measured of the targeting group to generate and collect a last set of two scattering signals as depicted in diagram 716. In this embodiment the scattering signal associated with spot 751*c* is not used. This completes the examination of a vertically oriented targeting group 700.

Because the L-shaped three beam configuration is used, the orientation of the illumination beams does not need to be rotated to capture the horizontally extending targets. This is highly advantageous because no movement and no adjustment of the beams are required. Referring to FIG. 8, an example horizontally extending targeting group 800 is depicted. As before, targets are arranged having gratings parallel to the x-axis and y-axis. FIG. 8 depicts six exposure diagrams (811, 812, 813, 814, 815, 816) of a horizontally disposed targeting group 800 as it is illuminated to obtain metrology information. This group is a horizontal analog to vertical group 700. A first illumination is depicted 811 is performed using the same L-shaped pattern of illumination spots as FIG. 7 (here depicted as 751*a* (white spot), 751*b* (dark spot), 751*c* (dark spot)) to simultaneously illuminate a pair of targets (801, 804) with spots (e.g., 751*c*, 751*b*). Any scattering from spot 751*a* (white spot) can be ignored in these measurements. The two scattering signals (the ones associated with 751*b* and 751*c*) are collected using appropriate detector apparatus. As the three beams advance horizontally across the targeting group to another set of targets, scattering signals are generated by the illumination patterned depicted in diagram 812. Two additional scattering signals are collected (associated with 751*b*, 751*c*). The process continues with the three spots advancing across the targeting group to other targets generating another set of scattering signals as depicted in diagram 813. As before, two resultant scattering signals are collected and measured. This continues until the entire target group or the desired targets are measured. This includes a shift in the targets inspected (see, diagrams 814-816) is measured. Finally, the spots illuminate the last targets desired to be measured collect a last set of two scattering signals as depicted in diagram 816. This completes the examination of a horizontally oriented targeting group 800.

One issue that may pose a difficulty using the embodiments depicted above is the fact that the polarization state of the illumination beam is the same for all targets measured. Thus, the polarization is parallel to one set of gratings (say, for example, the x oriented gratings) while being perpendicular to the other set of gratings (using the same example, the y oriented gratings). Under some circumstances, this can lead to non-optimal measurements relative to measurements that could have been obtained with the polarization having the same orientation relative to both gratings (i.e., both perpendicular or both parallel polarization relative the gratings). The inventors contemplate a targeting structure for use with simultaneous illumination that addresses this polarization issue.

Figure 9:
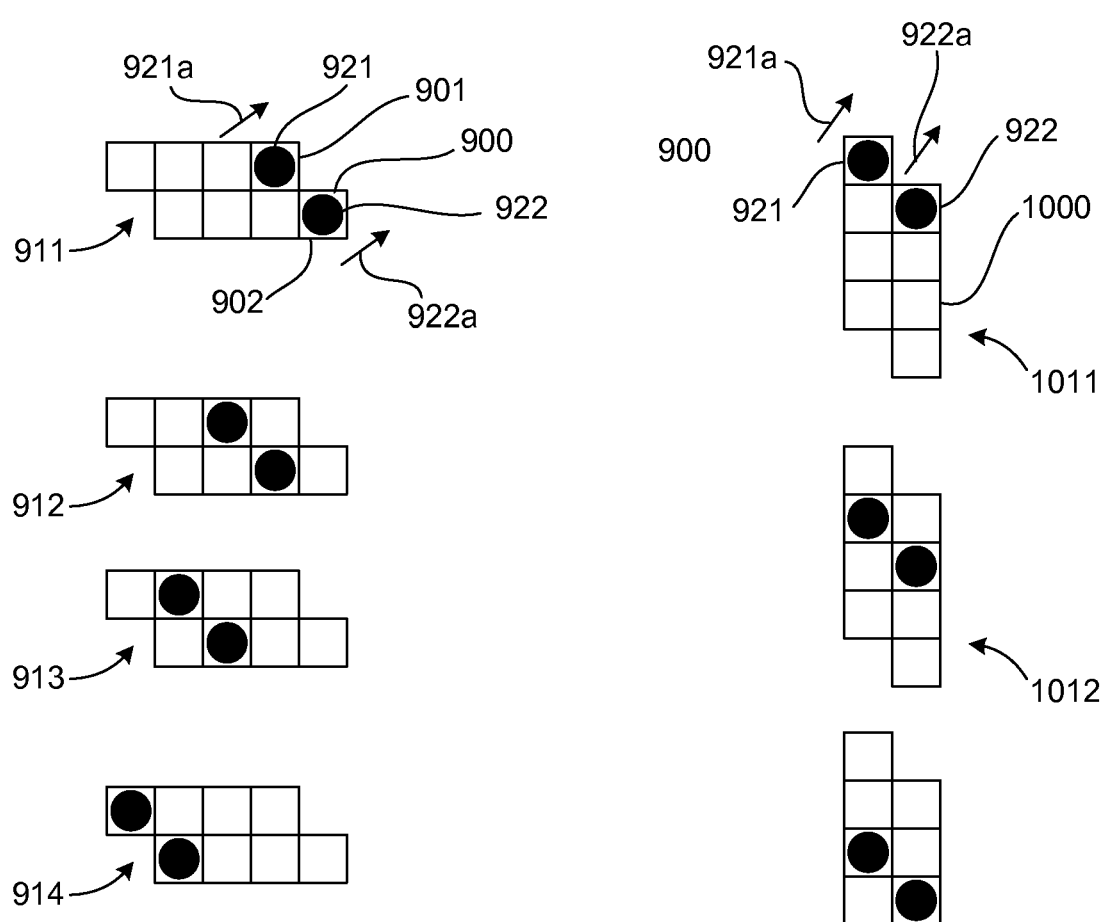
FIGS. 9 & 10 are simplified diagrams of horizontal and vertical targeting groups illustrating various inspection embodiments utilizing diagonally arranged inspection spots and staggered target groups to inspect target pairs in accordance with an embodiment of the invention.

In such an embodiment, only two illumination spots are required. FIG. 9 depicts one method and target group structure for addressing this issue. The target groups 900 are constructed in two staggered rows of targets. The targets in this embodiment are arranged so that the gratings are either parallel to or perpendicular to the depicted axes of the target group. For example, in the depicted embodiment the axes are parallel to x and y axes. Thus, the gratings are x or y oriented. The amount of stagger in the rows of targets is such that the targets are diagonal from one another as depicted. This generally means that if the target dimension for an individual target is say 2a, then the offset or stagger between the targets of the two rows is about one target dimension. Thus, the stagger is about 2a to enable a diagonal arrangement between targets. Accordingly, the illumination spots are diagonally directed onto the targeting group such that they are at a 45° angle from the axis of the wafer (and hence the targeting group). Here the inventors define the axis of the wafer as being defined by the saw streets of the wafer. Referring again to FIG. 9, the staggered rows of targets are arranged so that two illumination dots 901 & 902 are oriented at a 45° angle from the axis of the target (here the axis being the long axis or x-axis of the targeting group). Additionally, the axis of polarization is oriented at a 45° angle from the grating axes of the target (here the axis being the long axis or x-axis of the targeting group). Thus, a first illumination dot 901 impinges a first target 921 and a second illumination dot 902 impinges a second diagonally disposed target 922. The polarization axis is depicted for each of the dots. Polarization axis 921*a* corresponds to dot 921. Polarization axis 922*a* corresponds to dot 922. Both polarization axes (921*a*, 922*a*) are at 45 degree angles from the grating axes of the target regardless of whether the gratings are parallel to the x-axis of parallel to the y-axis. Thus, the polarization for each beam is identical regardless of the orientation of the axis of the target gratings. Thus, the difficulties encountered when illumination polarization changes from target to target are removed by this implementation.

Each of the four exposure diagrams 911, 912, 913, 914 shows the beam pair as it illuminates the targets of the group to obtain metrology information. The first illumination 911 is performed using two light spots 921 and 922 to simultaneously illuminate targets 901 and 902 to obtain and collect two scattering signals that can be measured using appropriate detector apparatus. The beams (spots 921, 922) advance across the targeting group to another set of targets as shown in diagrams 912, 913, 914. This continues until the entire target group or a selected portion of the targets are measured. Once the final two scattering signals are collected using appropriate detector apparatus the examination of the horizontally oriented targeting group is complete. As described above, the simultaneously illuminated targets can be a complementary target pairs, asymmetric target pairs, or unrelated target pairs.

The inventors point out that the 45° orientation of the polarization of the dots can be obtained by rotating the wafer 45° from the wafer x or y axes. Alternatively, the illumination beams can be adjusted by rotating the apertures that produce the beams by 45° rotation of the apertures in the image plane. Thus, the staggered target orientation can be fully exploited.

Figure 10:
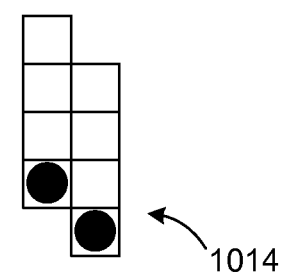

As with earlier embodiments, a wafer also includes vertically oriented targeting groups. Such are generally situated in the vertical saw streets. Such are illustrated in FIG. 10 which depicts an example vertical targeting group 1000 that extends in the vertical direction (here along the y-axis). As before, the illumination dots 921, 922 remain in the same orientation with the same 45° polarization orientation relative to the target gratings (e.g., 921a, 922a). Thus, diagrams 1011, 1012, 1013, 1014 depict the target group 1000 as the dots 921, 922 are scanned down the group to inspect each desired target while maintaining the 45° polarization orientation relative to the targets.

Figure 11:
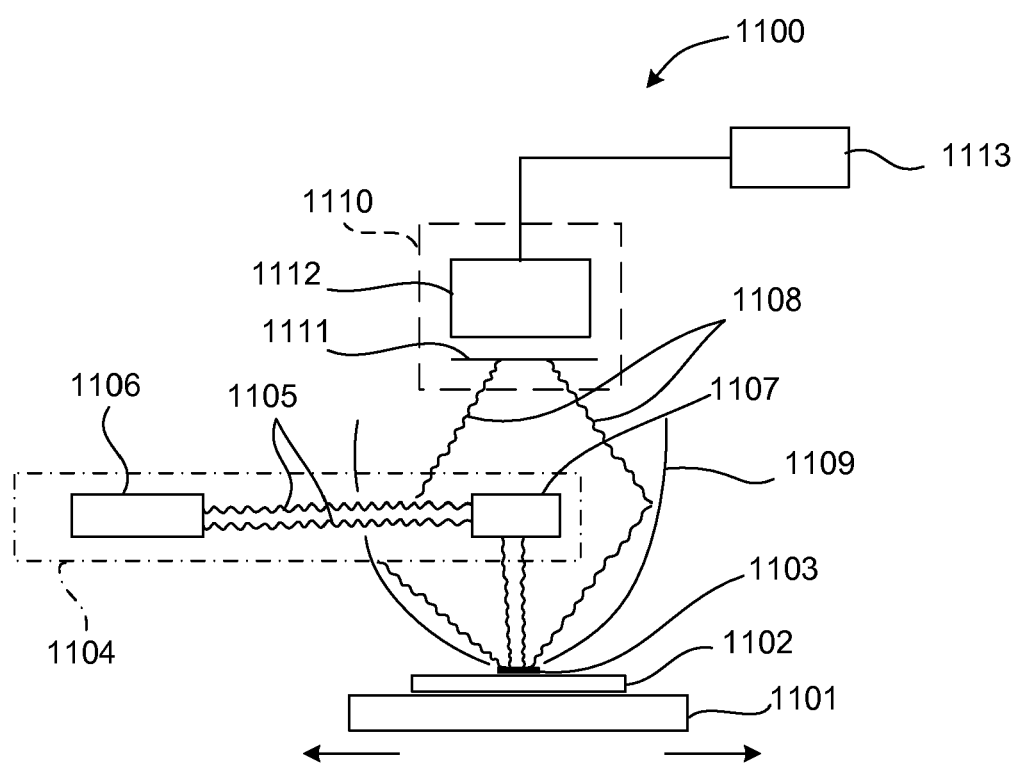
FIG. 11 is simplified diagram illustrating one embodiment of a multi-beam scatterometry inspection apparatus configured to inspect more than one target simultaneously in accordance with an embodiment of the invention.

FIG. 11 depicts one example implementation of an apparatus suitable for implementing the targeting schemes and methodologies disclosed herein. FIG. 11 shows a scatterometry overlay inspection apparatus 1100 including an examination platform 1101 for securing a wafer 1102 to enable positioning and movement of the wafer during inspection. In some embodiments a targeting group arranged along one axis is inspected and then the wafer is rotated 90 degrees to conduct an inspection of a corresponding target group arranged along a perpendicular axis. In alternative arrangements the beams are rotated 90 degrees using elements of an optical system to inspect the perpendicular target. The apparatus includes an illumination system 1104 for generating at least two light beams 1105 that can form spots on the targets 1103 of the wafer 1102. Such a system 1104 typically include an illumination source 1106 that produces a suitable optical beam (or a plurality of such beams). Such illumination sources 1106 typically are lasers but can include other sources such as filtered beams, LED's, and so on. The at least two light beams 1105 can be formed by directing light produced by the source through two or more apertures to produce beams as the light passes through the apertures. Such apertures can include an L-shaped set of apertures arranged to enable the three beam embodiments discussed herein. As an alternative, the light sources of the illumination system can be input into two or more optical fibers that can be used to direct the optical beams onto the selected targets 1103. Additionally, if desired the illumination system can include mechanisms suitable for enabling the rotation of the light beams. For example, the apertures can be rotated to change the orientation of the beams. Moreover, the illumination system 1106 generally includes a polarizer or other polarization system (e.g., a Wollaston prism as will be discussed later) to impart polarization on the beams 1105. The illumination system 1106 can also include optical for focus, demagnification, as well as other optical adjustments if desired.

Included as part of the illumination system (or in some embodiments included as separate from the illumination system) is an optical system 1107 configured to simultaneously direct the at least two light beams 1105 onto the at least two targets 1103 of the scatterometry targeting array formed on the wafer 1102 to generate at least two associated scattering signals 1108. In one example, the optical system 1107 simply comprises at least two optical fibers that direct the beams from the source 1106 to a location proximal to the targets 1103 to effectuate the formation of desired illumination spots. Typically, the optical system 1107 includes focusing and demagnifying optics to enable desired optical performance in the system. Other typical embodiments include mirrors and other beam direction optics that enable the beams to form precisely configured and accurately positioned light spots on the targets.

The system further includes a second collection optical system 1109 (depicted here as an optical reflector) for collecting the scattering signal 1108 produced by the illuminated targets 1103 and directing the scattering signal into a detection system 1110. The collection optical system 1109 can comprise any suitable type of collection optical system including, but not limited to, refractive optical systems and reflective optical systems.

The at least two associated scattering signals 1108 are directed into a detection system 1110 that commonly includes a spectrometer 1111 and a detector 1112. Such spectrometers 1111 can include, but are not limited to, analyzers or gratings and the like. Moreover, the detectors 1112 can be any commonly available light detection apparatus. Typical of such tools are photomultiplier tubes (PMT's), sensor arrays, and the vast array of other light detection tools known to those having ordinary skill in the art. It is pointed out that position sensitive filtering and position sensitive detectors enable the scattering signal to be selectively detected as originating from a specific illumination beam and/or target. Additionally, detection system 1110 embodiments comprising more than one detector 1112 and more than one spectrometer are contemplated by the inventors. The collected scattering signals are detected by the detection system which processes the signal using a processing unit 1113. Such processing units can be located locally or at remote locations. They can be connected with the system directly of indirectly with any number of networked implementations. Moreover, the processors themselves can be single microprocessors or CPU's as well as networked computer systems or even mainframe implementations as well as all related implementations. Such systems can present results graphically as images over a monitor, or data files, or any other format known to those having ordinary skill in the art.

Figure 12:
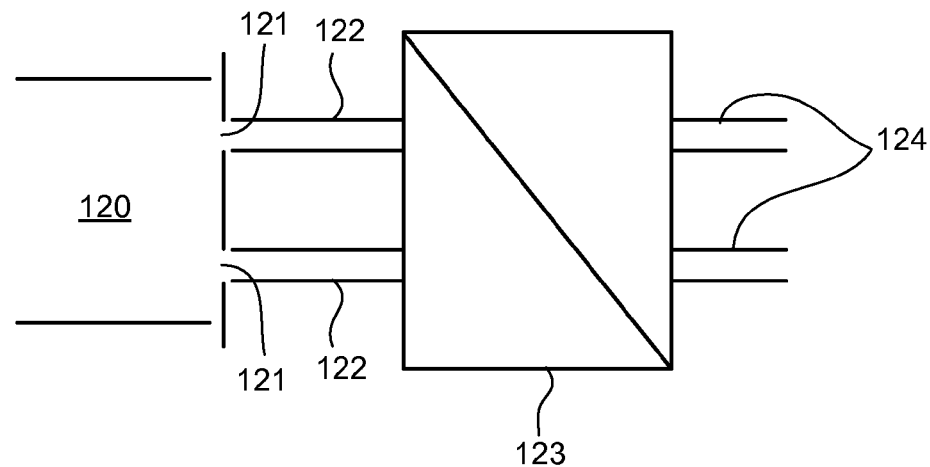
FIGS. 12 & 13 are simplified diagrams of optical beam generating optics suitable for employment with the embodiments of the invention.

FIG. 12 presents one example implementation of a portion of an illumination system such as depicted in 1106 of FIG. 11. An illumination beam 120 is directed through a plurality of apertures 121 to generate a plurality of light beams 122. The light beams are directed into a polarizer 123 to generate a plurality of similarly polarized illumination beams 124 that are projected onto selected targets on the wafer. In some embodiments this system can be rotated 90 degrees to enable inspection of perpendicular targets. Alternatively, in fiber embodiments the fibers can be rotated 90 degrees to enable inspection of perpendicular targets. Also, as discussed above, the target itself can be rotated 90 degrees if desired.

Figure 13:
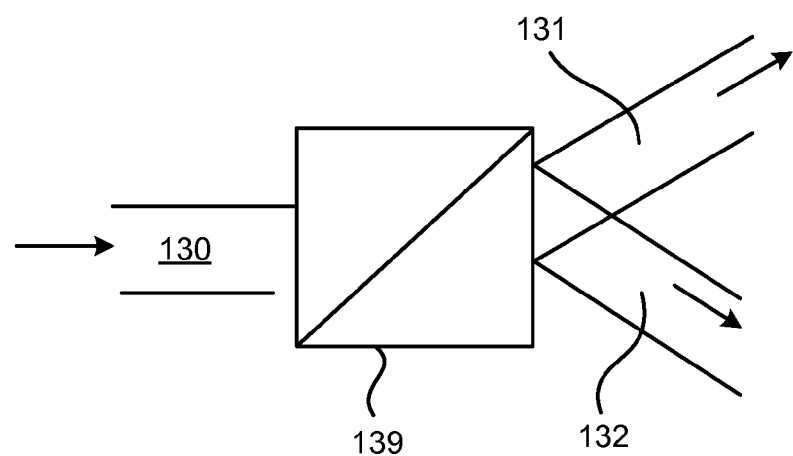

FIG. 13 presents an alternative apparatus for producing illumination beams. FIG. 13 again presents, for example, a portion of an illumination system such as depicted in 1106 of FIG. 11. An unpolarized illumination beam 130 (much the same as beam 120 described above) is directed through a Wollaston prism 139 to generate a pair of orthogonal, linearly polarized outgoing beams 131 & 132. For example, beam 131 can be S-polarized and beam 132 can be P-polarized. The light beams 131, 132 are directed onto the targets to produce scattering signals. As is known to those having ordinary skill in the art the outgoing light beams diverge from the prism with the angle of divergence determined by the prisms' wedge angle and the wavelength of the light. Commercially available prisms are available with divergence angles from 15° to about 45°. In accordance with embodiments described earlier, where a first target has a grating perpendicular to the grating of a second target, one of the beams is projected onto a first target having a polarization angle to the grating of, for example, +45° whereas the other beam (having a 90° difference in polarization angle) is directed onto the second target having a polarization angle to the grating of, for example, −45°. This enables both beams to impinge the target with essentially the same polarization angle relative to the target. This enables this embodiment to overcome polarization dependent inconsistencies in the scattering signal.

The invention disclosed here demonstrates many improvements over the state of the art and satisfies many of the needs in the industry as expressed in the foregoing paragraphs. Additionally, the present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors that many different metrology feature and defect feature arrangements and configurations can be established for targets constructed in accordance with the principles of the invention. Although only a few configurations are expressly disclosed herein, it should be appreciated by anyone having ordinary skill in the art that, using the teachings disclosed herein, many different configurations can be implemented and still fall within the scope of the claims. Further, reference in the claims to an element in the singular is not intended to mean "one and only one" unless explicitly stated, but rather, "one or more". Furthermore, the embodiments illustratively disclosed herein can be practiced without any element that is not specifically disclosed herein.

We claim:

1. A method of conducting scatterometry measurements using simultaneous target illumination with a plurality of illuminating light beams, the method comprising:
    providing a substrate with at least two scatterometry overlay, SCOL, target groups, wherein each target group has a long axis that extends along the length of the target group and wherein a first target group and a second target group are arranged such that a long axis of the target group is arranged perpendicular to a long axis of the second target group;
    simultaneously directing a set of three illumination beams onto the substrate to form an illumination dot pattern such that an arrangement of two perpendicular dot pairs are formed with each pair sharing a common dot and wherein a first dot pair defines an illumination axis that is perpendicular to an illumination axis of a second dot pair;
    directing the first dot pair onto the first target group such that the illumination axis of the first dot pair is perpendicular to the long axis of the first target group and each dot of the first dot pair illuminates a target of the first target group to produce at least two associated scattering signals associated with each illuminated target of the first target group,
    measuring the scattering signals associated with the first dot pair and the first target group;
    directing the second dot pair onto the second target group such that the illumination axis of the second dot pair is perpendicular to the long axis of the second target group and each dot of the second dot pair illuminates a target of the second target group to produce at least two associated scattering signals associated with each illuminated target of the second target group;
    measuring the scattering signals associated with the second dot pair and the second target group; and
    processing measurements of at least two associated scattering signals to obtain scatterometry metrology information.

2. A method of conducting scatterometry measurements using simultaneous target illumination with a plurality of illuminating light beams, the method comprising:
    providing a substrate with scatterometry overlay, SCOL, target groups that include a first and a second target group arranged with a long axis of the first target group arranged perpendicular to a long axis of the second target group, wherein each target group comprises at least two rows of SCOL targets extending along the long axis of the target group;
    simultaneously directing at least two illumination beams onto targets of the first target group such that an illumination dot is directed onto a target of each row of the first target group to generate associated scattering signals;
    changing the orientation of one of the substrate or the at least two illumination beams by effecting a 90 degree rotation;
    simultaneously directing the at least two illumination beams onto targets of the second target group such that an illumination dot is directed onto a target of each row of the second target group to generate associated scattering signals;
    measuring the associated scattering signals of the first and second target groups;
    processing measurements of scattering signals from the first and second target groups to obtain scatterometry metrology information.

3. A method of conducting scatterometry measurements using simultaneous target illumination with a plurality of illuminating light beams, the method comprising:
    providing a substrate with scatterometry overlay, SCOL, target groups that include a first and a second target group arranged with a long axis of the first target group arranged perpendicular to a long axis of the second target group, wherein each target group comprises at least two rows of SCOL targets extending along the long axis of the target group;
    simultaneously illuminating pairs of non-adjacent targets of a first row of the first target group with a pair of illumination dots to generate pairs of simultaneously generated associated scattering signals;
    simultaneously illuminating further pairs of non-adjacent pairs of a second row of the first target group with the pair of illumination dots to generate further pairs of associated scattering signals until a desired number of targets of the first target group have been inspected;
    changing an orientation of one of substrate or an orientation of the at least two illumination beams by effecting a 90 degree rotation;
    simultaneously illuminating further pairs of non-adjacent targets of a first row of the second target group with the pair of illumination dots to generate further pairs of associated scattering signals;
    simultaneously illuminating further pairs of non-adjacent targets of a second row of the second target group with the pair of illumination dots to simultaneously generate further pairs of associated scattering signals until a desired number of targets of the second target group have been inspected;
    measuring all of the scattering signals generated by illumination of the first and second target groups; and processing measurements of at least two associated scattering signals to obtain scatterometry metrology information.

4. A method of conducting scatterometry measurements using simultaneous target illumination with a plurality of illuminating light beams, the method comprising:

providing a substrate with scatterometry overlay, SCOL, target groups that include a first and a second target group arranged with a long axis of the first target group perpendicular to a long axis of the second target group, wherein each target group comprises at least two staggered rows of SCOL targets extending along the long axis of the target group with the staggered rows offset by one target dimension;

simultaneously directing at least two illumination beams onto diagonally arranged targets of the first target group such that two illumination dots are oriented at a 45 degree angle from the long axis of the first target group, one of the dots has a polarization state of +45 degrees relative to a grating orientation of one of the targets, the other dot has a polarization state of −45 degrees relative to a grating orientation of another one of the targets, one illumination dot is directed onto a target of a first row of the first target group and the other illumination dot is directed onto a target of a second staggered row of the first target group to illuminate said targets to generate a pair of associated scattering signals, simultaneously illuminating further diagonally arranged pairs of targets of the first targeting group with the pair of illumination dots to simultaneously generate further pairs of associated scattering signals until a desired number of targets of the first target group have been inspected;

simultaneously directing at least two illumination beams onto diagonally arranged targets of the second target group such that the two illumination dots are oriented at a 45 degree angle from the long axis of the first target group, one of the dots has a polarization state of +45 degrees relative to a grating orientation of one of the targets, the other dot has a polarization state of −45 degrees relative to a grating orientation of another one of the targets, one illumination dot is directed onto a target of a first row of the second target group and the other illumination dot is directed onto a target of a second staggered row of the second target group to illuminate said targets to generate a pair of associated scattering signals simultaneously illuminating further diagonal arranged pairs of the second target group to produce associated scattering signals until all desired targets of the second target group are inspected; and processing measurements of at least two associated scattering signals to obtain scatterometry metrology information.

* * * * *